United States Patent
Tethrake et al.

(10) Patent No.: US 7,213,767 B2
(45) Date of Patent: May 8, 2007

(54) SLEEVE-TYPE RFID TAG

(75) Inventors: Steven M. Tethrake, Collierville, TN (US); Robert Varner, Germantown, TN (US); Jeffrey H. Nycz, Collierville, TN (US); Paul Elliott, Collierville, TN (US)

(73) Assignee: SDGI Holding, Inc., Wilmington, DE (US)

( * ) Notice: Subject to any disclaimer, the term of this patent is extended or adjusted under 35 U.S.C. 154(b) by 0 days.

(21) Appl. No.: 11/063,844

(22) Filed: Feb. 23, 2005

(65) Prior Publication Data

US 2006/0186210 A1   Aug. 24, 2006

(51) Int. Cl.
   *G06K 19/06* (2006.01)
(52) U.S. Cl. .................. 235/492; 235/487
(58) Field of Classification Search ........... 235/487, 235/492; 340/572.1–572.9
   See application file for complete search history.

(56) References Cited

U.S. PATENT DOCUMENTS

| | | | |
|---|---|---|---|
| 4,075,632 A | 2/1978 | Baldwin et al. | |
| 4,360,801 A | 11/1982 | Duhame | |
| 4,390,880 A | 6/1983 | Henoch | |
| 4,463,353 A | 7/1984 | Kuzara | |
| 4,739,328 A | 4/1988 | Koelle et al. | |
| 4,952,913 A | 8/1990 | Pauley et al. | |
| 4,962,369 A | 10/1990 | Close | |
| 5,030,807 A | 7/1991 | Landt et al. | |
| 5,108,822 A * | 4/1992 | Imaichi et al. | 428/209 |
| 5,512,879 A | 4/1996 | Stokes | |
| 5,682,143 A | 10/1997 | Brady et al. | |
| 5,732,495 A | 3/1998 | Lowe et al. | |
| 5,742,618 A | 4/1998 | Lowe | |
| 5,884,425 A * | 3/1999 | Baldwin | 40/638 |
| 5,962,834 A | 10/1999 | Markman | |
| 5,973,600 A * | 10/1999 | Mosher, Jr. | 340/572.8 |
| 6,104,291 A | 8/2000 | Beauvillier et al. | |
| 6,104,295 A | 8/2000 | Gaisser et al. | |
| 6,118,379 A * | 9/2000 | Kodukula et al. | 340/572.8 |
| 6,255,949 B1 | 7/2001 | Nicholson et al. | |
| 6,280,544 B1 | 8/2001 | Fox et al. | |
| 6,406,579 B1 | 6/2002 | De Vaujany | |
| 6,598,800 B1 | 7/2003 | Schmit et al. | |
| 6,836,215 B1 * | 12/2004 | Laurash et al. | 340/572.1 |
| 6,963,351 B2 * | 11/2005 | Squires et al. | 347/214 |
| 2001/0018918 A1 | 9/2001 | Burnside et al. | |

(Continued)

FOREIGN PATENT DOCUMENTS

FR    2 740 109    4/1997

(Continued)

OTHER PUBLICATIONS

ChampionChip[online], [retrieved on Mar. 3, 2004]. Retrieved from the Internet: <URL: http:www.championchip.com/chips/index.php, (pp. 8).

*Primary Examiner*—Daniel Stcyr
*Assistant Examiner*—Jamara A. Franklin
(74) *Attorney, Agent, or Firm*—Hunton and Williams LLP

(57) ABSTRACT

An RFID tag that is integrated into a substantially cylindrically-shaped structure that can be attached to an object to be identified through radio frequency identification techniques by sliding the substantially cylindrically-shaped structure over at least a portion of the object.

28 Claims, 2 Drawing Sheets

U.S. PATENT DOCUMENTS

2003/0102978 A1* 6/2003 Schwandner ............ 340/693.5
2004/0006445 A1   1/2004 Paek

FOREIGN PATENT DOCUMENTS

| | | |
|---|---|---|
| JP | 2002/222405 | 8/2002 |
| JP | 2003/052717 | 2/2003 |
| JP | 2003/140725 | 5/2003 |
| JP | 2003/141650 | 5/2003 |

* cited by examiner

SLEEVE-TYPE RFID TAG

FIELD OF THE INVENTION

Embodiments of the invention generally relate to radio frequency identification systems, and more particularly to a sleeve-type, or substantially cylindrically-shaped RFID transponder tag for easy attachment, detachment and reattachment to a variety of different shaped devices and equipment. The sleeve-type or substantially cylindrically-shaped RFID transponder tag may be particularly suited for application to medical and surgical devices and equipment.

DESCRIPTION OF RELATED ART

Electronic data carrying memory devices are known. These devices provide a means for tracking and providing information about tools, equipment, inventory and other items. Memory devices permit linking of large amounts of data with an object or item. They typically include a memory and logic in the form of an integrated circuit ("IC") and a mechanism for transmitting data to and/or from the product or item attached to the memory device. An example of such a memory device-based product identification technology is radio frequency identification (RFID).

Radio frequency identification (RFID) systems use an RF field generator (reader) and a plurality of RFID transponder tags that store information about the goods and products to which they are attached. RFID tags are miniature electronic circuits that typically consist of a coil that acts as an antenna and a small silicon-based microprocessor with a memory, all encapsulated in a sealing material. RFID tags store identification information, usually in the form of an identification number that corresponds to an object or item to which the tag is attached. When a transponder tag enters an RF field generated by a reader device, the circuit of the tag becomes energized causing the processor to perform a data operation, usually by emitting a signal containing the processor's stored information. The basic structure and operation of RFID tags can be found in, for example, U.S. Pat. Nos. 4,075,632, 4,360,801, 4,390,880, 4,739,328 and 5,030,807, the disclosures of which are hereby incorporated by reference in their entirety.

RFID tags generally are formed on a substrate, such as, for example, paper, and can include analog RF circuits, digital logic, and memory circuits. RFID tags also can include a number of discrete components, such as capacitors, transistors, and diodes. RFID tags are categorized as either active or passive. Active tags have their own discrete power source such as a battery. When an active tag enters an RF field it is turned on and then emits a signal containing its stored information. Passive tags do not contain a discrete power source. Rather, they become inductively or capacitively charged when they enter an RF field. Once the RF field has activated the passive circuit, the passive tag emits a signal containing its stored information. Passive RFID tags usually include an analog circuit that detects and decodes the interrogating RF signal and that provides power from the RF field to a digital circuit in the tag. The digital circuit generally executes all of the data functions of the RFID tag, such as retrieving stored data from memory and causing the analog circuit to modulate to the RF signal to transmit the retrieved data. In addition to retrieving and transmitting data previously stored in the memory, both passive and active dynamic RFID tags can permit new or additional information to be stored in the RFID tag's memory, or can permit the RFID tag to manipulate data or perform some additional functions.

Though originally invented to track feeding of cattle, RFID tags are today utilized in a variety of applications including retail security, inventory management, and even computerized checkout. With the price of RFID tags now reaching as low as 5 cents per tag, and because of reductions in size due to an overall trend towards miniaturization in circuit design, RFID tags currently are being applied to many types of products, both at the consumer level as well as in manufacturing processes. RFID tags enable manufacturers to wirelessly track products from the manufacturing stage to the point-of-sale. They provide a robust, cost effective, efficient and accurate solution to inventory tracking and management.

Current commercially available RFID tags, both active and passive, generally come in one of two configurations: inductively or capacitively coupled. Inductively coupled tags, the first type of RFID tags developed, consist of a silicon-based microprocessor, a metal coil wound into a circular pattern which serves as the tag's antenna, and an encapsulating material that wraps around the chip and coil. These tags are powered by an electromagnetic field generated by the tag reader. The tag's antenna picks up the electromagnetic energy which in turn powers the chip. The tag then modulates the electromagnetic field in order to transmit data back to the reader. Despite advances in silicon manufacturing processes, inductively coupled tags have remained relatively expensive due to the coil antenna and the manufacturing process required to wind the coil around the surface of the tag.

The second type of RFID tags are capacitively coupled RFID tags. Capacitively coupled tags eliminate the metal coil, consisting instead of a silicon microprocessor, paper substrate, and a conductive carbon ink that is applied to the paper substrate through a conventional printing means. By using conductive ink and conventional printing processes, a relatively low cost, disposable tag can be created that is easily integrated into conventional product labels.

RFID tags are rapidly becoming the preferred method of inventory tracking in retail and distribution applications and will likely surpass bar codes as the preferred point-of-sale checkout identifier. Large retail chains such as WALMART Corporation are already requiring their suppliers to utilize RFID tags for tracking shipments. RFID tags have significant advantages over bar code labels. For example, bar codes are limited in size by resolution limitations of bar code scanners, and the amount of information that the symbols can contain is limited by the physical space constraints of the label. Therefore, some objects may be unable to accommodate bar code labels because of their size and physical configuration. In contrast, RFID tags store their information in digital memory. Thus, they can be made much smaller than bar code tags.

Another advantage of RFID tags over bar codes is that bar code readers requires line of sight in order to read the reflection pattern from a bar code. As labels become worn or damaged, they can no longer be read with the bar code scanner. Also, because a person operating the bar code scanner must physically orient either the scanner or the product to achieve line of sight on each item being scanned, items must be scanned one at a time resulting in prolonged scan time. RFID tags, on the other hand, are read through radio waves, which do no require line of sight because they are able to penetrate light impermeable materials. This not only eliminates the line of sight requirement, but also allows rapid identification of a batch of tagged products.

Yet another relative advantage of RFID tags over bar code labels is that for dynamic RFID tags, the information stored in the tag may be updated using a writing device to wirelessly transmit the new information to be stored. Updating information in bar code tags typically requires printing a new tag to replace the old.

One problem associated with the use of RFID tags, which also is common to bar code tags, is that it can be difficult to securely attach the tags to various goods and products. As discussed above, capacitively coupled RFID tags usually are printed on a paper substrate and then attached to various items using an adhesive bonding. However, in some applications, a paper tag may not hold up to the rigors of the environment in which the product is used. For example, in the field of medical equipment, and in particular, surgical instruments and surgical instrument storage and sterilization systems, items are routinely exposed to environments containing various combinations of high temperatures, high pressure and liquid, vaporous and/or gaseous chemical sterilants. Over time, a paper RFID tag would not provide reliable performance under these harsh conditions. More rugged RFID tags have been developed as a potential solution to this problem. An example of a rugged RFID tag is provided in U.S. Pat. No. 6,255,949, the disclosure of which is hereby incorporated by reference in its entirety. The '949 patent discloses an RF transponder tag surrounded by a thermally resistant polymer and encapsulated in a hardened case. Because radio frequency waves can penetrate such materials, performance of the tag is not degraded by the case or polymer. Such a configuration prevents damage to the transponder tag if exposed to high temperature environments.

While making the tag enclosure more rugged may sometimes protect the internal components of the tag, this still does not solve the problem of keeping the tag securely attached, particularly in harsh environments. As discussed above, substrate based tags, even ruggedized tags, are typically mounted using an adhesive. This presents at least two problems for the application of tags exposed to harsh environments. First, adhesives will break down and lose their adhesive property when they are exposed to heat and moisture. This limits their usage to dry "friendly" environments. Second, adhesives typically require a flat surface on which to mount the RFID tags. This precludes the mounting of tags onto devices, equipments, or containers that do not have a flat surface of sufficient dimensions. Furthermore, many items do not have geometrically shaped portions sufficiently large to accommodate such a substrate based tag. Thus, for at least these reasons, adhesives do not provide an effective solution for attaching RFID tags in certain environments.

A proposed solution to the above described attachment problem has been to integrate the RFID tag into a bracelet or strap. This can be particularly useful for patient or personal monitoring systems. U.S. Pat. No. 6,104,295 describes such an electronic band having an integral RFID tag. However, a problem with this solution is that the band's width will preclude application of the bracelet to small items. Also, because the portion of the band defined by the tag is rigid, this will dictate the minimum width that the band strap can be adjusted to. Thus, for items having a small diameter, only a loose fitting will be possible.

The problems of attachment as well as ruggedization are particularly acute in the field of medical equipment and instruments. Surgical equipment, including surgical instruments, kits and other medical equipment must be regularly exposed to heat as well as liquid and/or vaporous chemicals during the sterilization process. Also, this equipment is typically expensive and highly mobile. Thus, there is a strong need for accurate and efficient tracking that does not impede or interfere with the sterilization process.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

Based on the foregoing, it would be desirable to provide an RFID tag that overcomes or ameliorates some or all of the shortcomings of conventional tags. In particular, it would be desirable to provide an RFID tag that can withstand the rigors of sterilization and other harsh environments and that can also be cheaply and easily used with new as well as existing instruments and equipment.

Thus, it is a feature of various embodiments of the invention to provide an RFID tag that is sufficiently ruggedized to permit use of the tag in moist, heated, cooled, pressurized or other destructive environments. It is a further feature of various embodiments of the invention to provide an RFID tag that does not require modification to existing objects to be retroactively compatible.

Another feature of various embodiments of the invention provides an RFID tag that can be attached to objects of differing shapes. An additional feature of various embodiments of the invention provides an RFID tag that is operable to be affixed to various objects without adhesives.

To achieve the above-noted features, and in accordance with the purposes as embodied and broadly described herein, one exemplary embodiment provides a substantially cylindrically-shaped RFID tag. The substantially cylindrically-shaped RFID tag according to this embodiment comprises a substantially cylindrically-shaped structure, and an RFID transponder circuit secured to the substantially cylindrically-shaped structure.

In accordance with another exemplary embodiment, a reusable RFID tag is provided. The reusable RFID tag according to this embodiment comprises a substantially cylindrically-shaped structure, and an RFID circuit secured to the substantially cylindrically-shaped structure.

In accordance with a further exemplary embodiment, a method of manufacturing a reusable RFID identification tag is provided. The method according to this embodiment comprises encasing an RFID transponder circuit in a substantially cylindrically-shaped structure.

These and other embodiments and advantages of the present invention will become apparent from the following detailed description, taken in conjunction with the accompanying drawings, illustrating by way of example the principles of the invention.

BRIEF DESCRIPTION OF THE DRAWINGS

Purposes and advantages of the embodiments will be apparent to those of ordinary skill in the art from the following detailed description in conjunction with the appended drawings in which like reference characters are used to indicate like elements, and in which.

DETAILED DESCRIPTION

Figure 1:
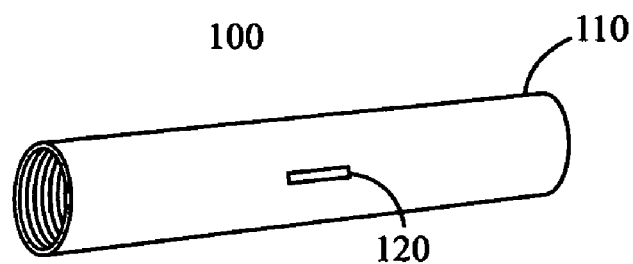
FIG. 1 is a perspective view of an exemplary sleeve-type RFID tag according to various embodiments.

The following description is intended to convey a thorough understanding of the embodiments described by providing a number of specific embodiments and details involving a sleeve-type RFID transponder tag and method of manufacturing a sleeve-type RFID transponder tag. It is understood, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments, depending upon specific design and other needs.

As used herein, the expressions "RFID tag" and "RFID transponder tag" will refer to any active or passive type of electronic data storage device, read-only or read and write, that is wirelessly activated in the presence of a radio frequency (RF) field, including any currently available inductively coupled RFID tags, capacitively coupled RFID tags and even future RF-type tags not yet available. This includes tags operating in the 125 kHz, 13.56 MHz, 868–927 MHz, 2.45 GHz and 5.8 GHz frequency bands as well as other suitable frequency bands. Also, the tag may be a silicon-type IC tag, a printed tag printed with a conductive ink-based printing process or a tag formed by other suitable means.

As used herein, the expressions and terms "surgical instrument," "medical instrument," "instrument," or "device" will refer to any type of surgical or medical instrument or portable equipment or device to which it may be desirable to attach an RFID tag. Though the specification is written in the context of medical and/or surgical instruments, it should be appreciated that the sleeve-type RFID tag of the embodiments may be used with a variety of different items to be identified as shape and design constraints permit, including tools and equipment in other fields unrelated to the medical field. All of these uses are within the intended scope of the embodiments of the invention.

Through out this description, the expression "sleeve-type RFID tag" will be given broad meaning including, but not limited to, any type of RFID transponder tag that is encapsulated between layers of a sleeve that can be stretched and slid over a portion of an item to be tagged and held in place by friction. In various other embodiments, the tag will be formed over a portion of an instrument or device to be tagged, such as, for example, the handle of the instrument or device, during the later stages of the manufacturing process thereby eliminating the need to embed the tag in the device.

Described above are certain problems associated with the use of RFID tags on medical and/or surgical instruments. One proposed solution to the problem of RFID tags for surgical instruments and other surgical equipment has been to embed RFID transponder tags in a portion of the instrument at the time of manufacture. While ideal in theory, this solution may still suffer from some practical difficulties. First, this approach requires the tool or instrument to have been manufactured with the RFID tag inside. This is undesirable because it complicates the manufacturing process thereby increasing its expense, and it prohibits application of the technology to existing equipment through retrofitting. Second, the individual surgical instruments and equipment often have a high metal content. Because the tag is embedded in the metal, reading of the tag can be difficult due to losses in the metal of the electromagnetic signal. Finally, if the tag stops functioning, the entire instrument must be discarded, or else RF identification techniques can not be utilized with it. Thus, embedding still suffers from some significant technical obstacles.

Referring now to FIG. 1, a sleeve-type RFID transponder tag 100 is illustrated in accordance with at least one exemplary embodiment of this invention. As shown in FIG. 1, the sleeve-type RFID transponder tag 100 comprises a sleeve portion 110 and an RFID transponder circuit element 120. Preferably, the sleeve portion 110 is cylindrically shaped and is comprised of a flexible and resilient material. The RFID transponder circuit element 120 is shown as a visible element for purposes of example only. In practical applications, the circuit element 120 may appear externally as a bump, a recess, a color variation, thickness variation, or may be completely unidentifiable when looking at the tag 100 itself.

The preferably flexible resilient sleeve portion 110, though shown in the FIG. 1 as a single layer, may comprise a plurality of different layers having different conductive and physical properties. However, in various embodiments, it will be preferable for the sleeve portion 110 to have an outer layer made of a material such as rubber, silicone or other suitable material that is flexible, resilient and fluid impervious.

Though the tag's design will permit a single tag to be attached to devices of differing size, within the elastic limits of the tag, the tag may be manufactured in a plurality of different diameters and lengths to accommodate objects falling within various size and diameter ranges. The particular dimensions of the tag, including the ratio of the radius to the length, are not specific to the invention. In addition, the tag 100 shown in FIG. 1 is a cylindrical tag having a circular cross-section, although any cross-section can be used in the embodiments. Other embodiments include tags whose cross-section varies throughout the length, as well as whose radius varies throughout the length. The expression "substantially cylindrically-shaped structure" includes cylindrically shaped structures having a circular cross-section, as well as other shell-type structures having non-circular cross-sections (e.g., oval, rectangular, square, triangular, octagonal, hexagonal, etc.). Those skilled in the art will be capable of designing a suitable tag for any given instrument, using the guidelines provided herein.

Also, though not shown in FIG. 1, the outside surface 110 of the tag 100 may have various visual indicia printed thereon including a numeric indicia 112, such as a part or item identification number, a textual indicia 114, such as a product name or product category name, and a brand indicia 116, such as a manufacturer name of the RFID tag or the item to which the tag is attached. In various exemplary embodiments, all three indicia are utilized. However, in various other embodiments, less then three indicia are utilized. In still further embodiments, more than three indicia are utilized or no indicia at all are utilized. In addition to these embodiments, other embodiments may utilize color coding, bar coding or other optically recognizable indicia. The present invention is compatible with any of the aforementioned indicia schemes.

With continued reference to the sleeve-type RFID transponder tag 100 of FIG. 1, during practical application, an operator will slide the sleeve-type tag 100 over at least a portion of the object to be identified. The portion of the object preferably is slightly larger in diameter than the diameter of the tag 100 so that the both friction and the resilient property of the tag 100 will serve to secure the tag to the object. The RFID transponder tag 100 preferably is preprogrammed with identification information for the item to which it will be attached. Therefore, once tagged, the item may be wirelessly inventoried by activating the RFID transponder tag 100 using a suitable RF reader device. Because RFID reader devices are well known in the art, a detailed discussion of such devices has been intentionally omitted. The sleeve-type RFID transponder tag 100 according to the preferred embodiment is compatible with any suitable reader devices whether hand held, stationary, fixed or otherwise configured. Moreover, as will be discussed in greater detail herein, because the antenna portion of the tag circumscribes the tube-like opening defined by the tag 100, read failures due to improper orientation are greatly reduced and ideally eliminated.

Figure 2:
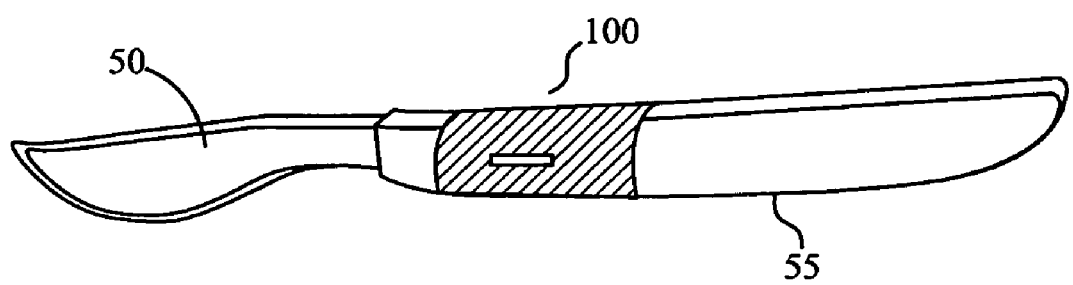
FIG. 2 is a perspective view of an exemplary sleeve-type RFID tag such as that illustrated in FIG. 1 attached to a surgical instrument.

Referring now to FIG. 2, FIG. 2 is a perspective view of an exemplary sleeve-type RFID tag such as that illustrated in FIG. 1 attached to a surgical instrument, in this case a two piece scalpel consisting of a blade 50 and handle portion 55. As shown in FIG. 2, to attach the tag 100 to the handle portion 55 of the scalpel, a user merely slides the sleeve portion 110 of the tag 100 over the distal end of the handle portion 55 up to a location on the handle portion 55 that will minimize obtrusion to the user of the scalpel. With a surgical instrument such as a scalpel the tag 100 intuitively fits over the handle portion 55. However, with other equipment, the tag 100 may be attached to a tube, cord, knob, protrusion, or other semi-cylindrical member of an item to be tagged. Alternatively, in various other exemplary embodiments, the tag 100 may be attached to an intervening cylindrically shaped tag fastener which is then secured to the item to be tagged using a cable, twist-tie or other suitable attachment means.

Figure 3:
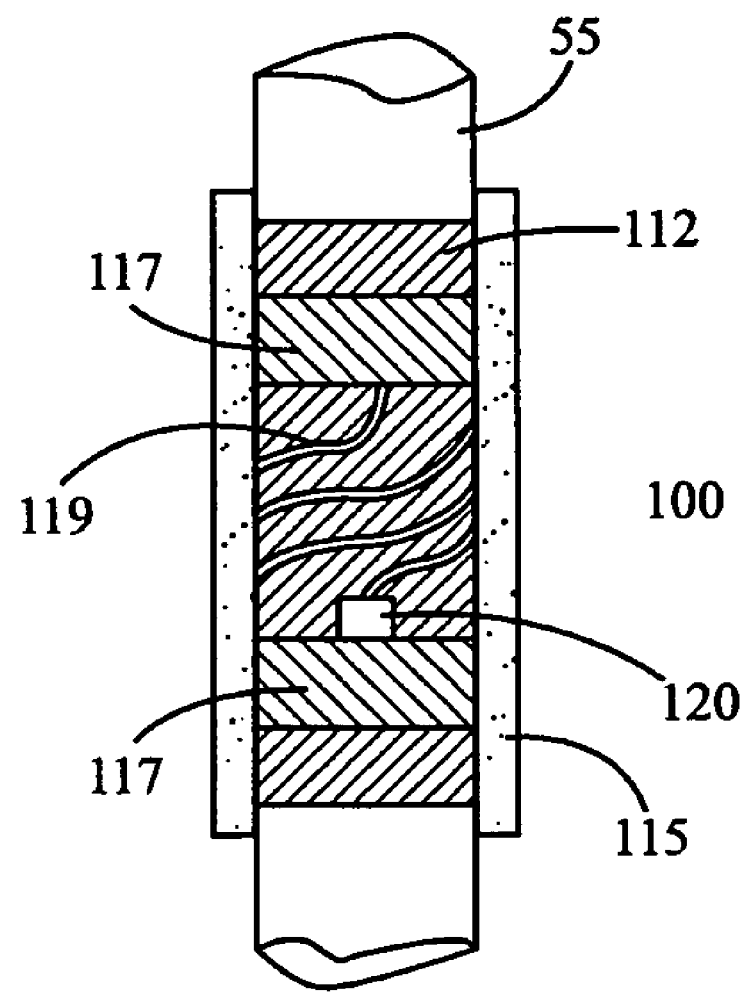
FIG. 3 is a cross-sectional diagram illustrating internal components of an exemplary sleeve-type RFID tag according to various embodiment.

Referring now to FIG. 3, a cross-sectional diagram illustrating internal components of an exemplary sleeve-type RFID tag according to various embodiment of this invention is shown. The tag 100 preferably is comprised of an insulating low loss dielectric substrate 112, and a conductive layer 117 comprising one or more conductive foil portions 117 and an antenna portion 119 that are connected to the tag housing 120. The dielectric substrate 112 will serve to insulate the electrical circuitry from current losses. Furthermore, in a preferred embodiment, the antenna 119 will circumscribe the opening of the tag 110 at least one time so as to enable reads from the tag irrespective of the instrument's orientation. Also, in a preferred embodiment, the RFID tag 120 is encased in a protective housing, such as, for example, a mini small outline package (MSOP) for integrated circuits or any other suitable protective housing that will protect the integrated circuit of the tag against compression damage. Finally, an outer layer 115 of plastic, rubber or silicone preferably encapsulates the internal components and layers, protecting them from the external environment. This outer layer 115 will provide a barrier to moisture, heat, cold etc. so as to protect the internal RFID tag and related circuitry of the conductive layer 117 and antenna 119 from damage caused by harsh environments, such as for example, during sterilization.

It should be noted that in the embodiments discussed thus far, the tag is contemplated as a separately manufactured stand-alone tag that is manually attached to instruments or other objects to be identified. However, it should be appreciated that alternatively, the tag may be manufactured in a permanent or semi-permanent manner subsequent to, or during the manufacturing process of the instrument or object. That is, the tag could be manufactured directly on the instrument or object using various automated manufacturing techniques known in the art. In such an embodiment, the layer closest to the object, i.e. the dielectric layer 112, or even another intervening layer, may be affixed to the instrument or object using an adhesive or may simply adhere to the object upon hardening. Alternatively, one or more layers of the tag 100 may be comprised at least in part of the same or similar material as the outermost surface of the instrument or object to be tagged. After the tag is formed on the instrument or object, the entire tag or even the entire object can be encapsulated with silicone or other sealing material providing a relatively simple, inexpensive and effective method of attaching tags to a instrument or object. In this manner, the tag could be integral with the instrument or object.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed is:

1. An RFID tag comprising:
   a resilient tubular sleeve portion; and
   an RFID transponder circuit comprising an antenna, a microprocessor and a memory structure secured to a surface of the resilient tubular sleeve portion, wherein the resilient tubular sleeve portion is open on at least one end and adapted to be slid around a portion of an object to be tagged and to conform to the shape of the portion of the object through resiliency, and the antenna circumscribes an opening defined by the resilient tubular sleeve portion at least one time.

2. The tag according to claim 1, wherein the resilient tubular sleeve portion comprises a plurality of layers.

3. The tag according to claim 2, wherein one of the plurality of layers is a low loss dielectric layer.

4. The tag according to claim 3, wherein the RFID transponder circuit is in contact with the low loss dielectric layer.

5. The tag according to claim 2, further comprising an outermost encapsulating layer.

6. The tag according to claim 5, wherein the outermost encapsulating layer is made of a flexible, moisture impervious material.

7. The tag according to claim 1, wherein the memory is operable to store identification information for the object that the tag is associated with.

8. The tag according to claim 1, wherein the antenna is a wire loop-type antenna.

9. The tag according to claim 1, wherein at least a portion of the RFID transponder circuit is encapsulated in a protective housing.

10. The tag according to claim 9, wherein the protective housing comprises a material selected from the group consisting of plastic, metal, metal alloy and other pressure resistant material.

11. The tag according to claim 9, wherein the protective housing is a mini small outline package (MSOP) for integrated circuits.

12. The tag according to claim 1, further comprising one or more visual indicia on an outward facing surface of the resilient tubular sleeve portion.

13. The tag according to claim 12, wherein the one or more indicia is selected from the group consisting of a brand owner name, a product name, a category name, a color code, a graphic image, a product identification number, a bar code and combinations thereof.

14. A reusable RFID tag comprising:
   a resilient tubular sleeve structure; and
   an RFID circuit comprising an antenna, a microprocessor and a digital memory structure, secured to the resilient tubular sleeve structure, wherein the resilient tubular sleeve structure is open on at least one end and adapted to be slid around an object to be tagged and to conform to the shape and of the object through resiliency, and the antenna circumscribes an opening defined by the resilient tubular sleeve portion at least one time.

15. The tag according to claim 14, wherein the resilient tubular sleeve structure comprises a plurality of layers.

16. The tag according to claim 15, wherein one of the plurality of layers is a low loss dielectric layer.

17. The tag according to claim 16, wherein the RFID circuit is in contact with the low loss dielectric layer.

18. The tag according to claim 14, wherein the digital memory is operable to store identification information for the object that the tag is associated with.

19. The tag according to claim 14, wherein the antenna is a wire loop-type antenna.

20. The tag according to claim 14, wherein at least the microprocessor and the memory are encapsulated in a protective housing.

21. The tag according to claim 20, wherein the protective housing comprises a material selected from the group consisting of plastic, metal, metal alloy and other pressure resistant material.

22. The tag according to claim 20, wherein the protective housing is an MSOP for integrated circuits.

23. The tag according to claim 14, further comprising a resilient outermost encapsulating layer surrounding the resilient tubular sleeve structure.

24. The tag according to claim 23, wherein the outermost encapsulating layer is made of a flexible, moisture impervious material.

25. The tag according to claim 14, further comprising one or more visual indicia on an outward facing surface of the substantially cylindrically-shaped structure.

26. The tag according to claim 25, wherein the one or more indicia is selected from the group consisting of a brand owner name, a product name, a category name, a color code, a graphic image, a product identification number, a bar code and combinations thereof.

27. A method of manufacturing a reusable RFID identification tag comprising:
   forming a predetermined length of resilient tubular material to create a resilient tubular sleeve structure having an opening at each end;
   attaching an RFID transponder circuit to a surface of the resilient tubular sleeve structure, the RFID circuit comprising an antenna, a processor and a digital memory structure, wherein attaching comprises encasing the antenna between layers of the resilient tubular sleeve structure so as to circumscribe the resilient tubular sleeve structure at least one time.

28. The method of claim 27, wherein attaching the RFID transponder circuit comprises encapsulating at least the processor and the digital memory in a protective housing and encasing the housing between layers of the resilient tubular sleeve structure.

* * * * *